(12) United States Patent
Doyle et al.

(10) Patent No.: US 9,958,321 B2
(45) Date of Patent: May 1, 2018

(54) TRANSVERSE OPTICAL TRANSMISSION PROBE

(71) Applicant: Axiom Analytical, Inc., Tustin, CA (US)

(72) Inventors: Walter M. Doyle, Tustin, CA (US); Norman A. Jennings, Tustin, CA (US)

(73) Assignee: HELLMA HOLDING GMBH, Muellheim (DE)

( * ) Notice: Subject to any disclaimer, the term of this patent is extended or adjusted under 35 U.S.C. 154(b) by 63 days.

(21) Appl. No.: 14/964,428

(22) Filed: Dec. 9, 2015

(65) Prior Publication Data

US 2016/0161335 A1 Jun. 9, 2016

Related U.S. Application Data

(60) Provisional application No. 62/089,525, filed on Dec. 9, 2014.

(51) Int. Cl.
*G01J 3/02* (2006.01)
*G01J 3/42* (2006.01)
*G01N 21/85* (2006.01)

(52) U.S. Cl.
CPC ........... *G01J 3/0218* (2013.01); *G01J 3/0291* (2013.01); *G01J 3/42* (2013.01); *G01N 21/8507* (2013.01); *G01N 2021/8528* (2013.01); *G01N 2021/8535* (2013.01)

(58) Field of Classification Search
CPC .......... G01J 3/0218; G01J 3/02; G01J 3/0291; G01J 3/42; G01N 21/8507; G01N 2021/8528; G01N 2021/8535
USPC ...................................... 250/227.23
See application file for complete search history.

(56) References Cited

U.S. PATENT DOCUMENTS

| 7,279,912 B2 * | 10/2007 | Leon ................. G01R 1/06738 324/755.11 |
| 8,694,069 B1 * | 4/2014 | Kosa ..................... A61B 5/1455 264/1.24 |

* cited by examiner

*Primary Examiner* — Seung C Sohn
(74) *Attorney, Agent, or Firm* — Myers Andras LLP; Joseph C. Andras

(57) ABSTRACT

A transverse optical transmission probe having a probe body and a probe tip. The probe use optical fibers to both transmit radiation from an instrument to the probe tip and to return the sample affected radiation to the instrument. The fibers are in parallel and contained in the probe body. The probe tip includes two optical elements that protrude into the sample and are configured to define a sample gap so that incident radiation pass through the sample in a direction transverse to the axis to the probe and eventually reaches the receiving fiber. Each of the optical elements may be formed from a single piece of material or may be a composite formed by adhering two or more pieces of material together. One or more lensed surfaces may be used to cause the end of the transmitting fiber to be imaged on the end of the receiving fiber.

23 Claims, 9 Drawing Sheets

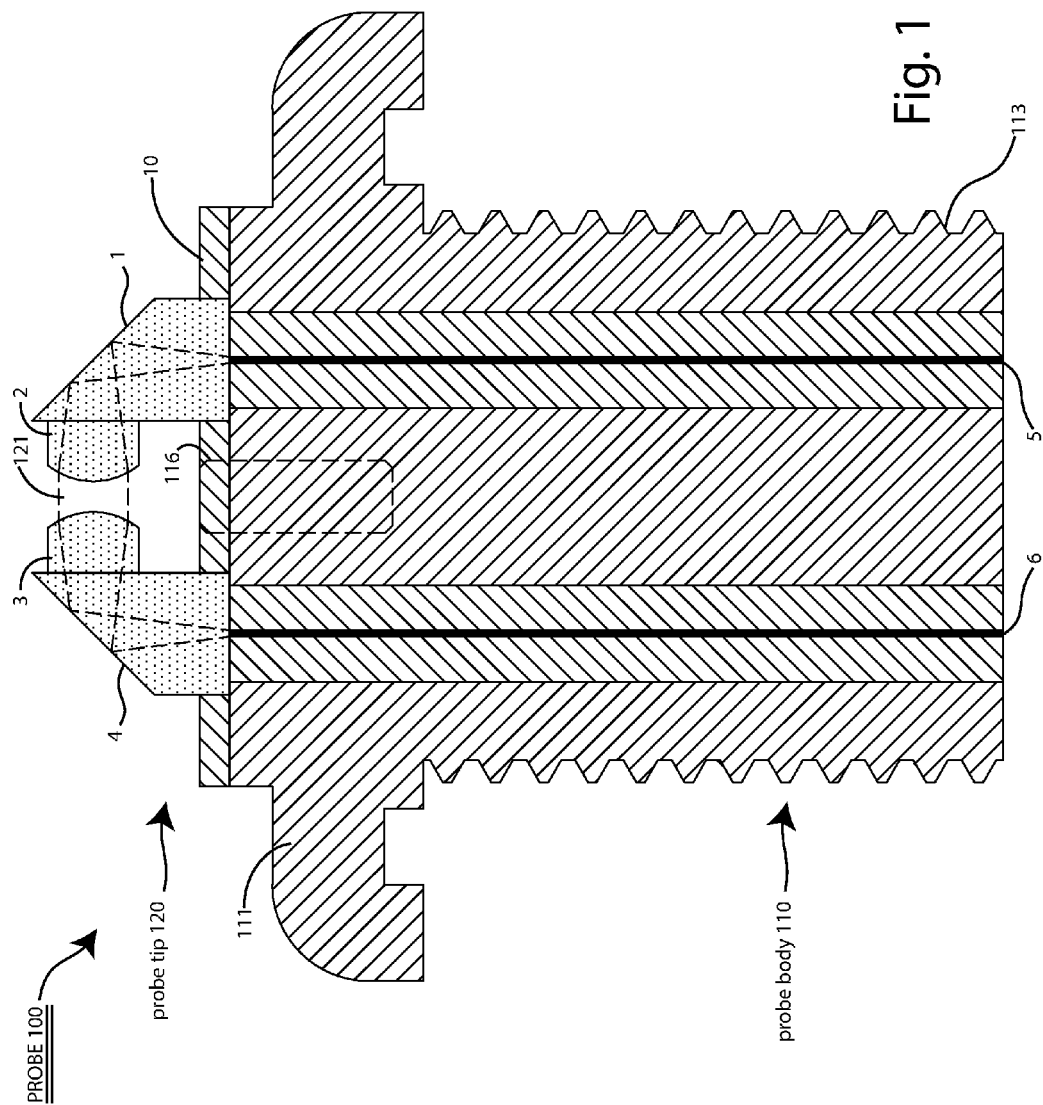

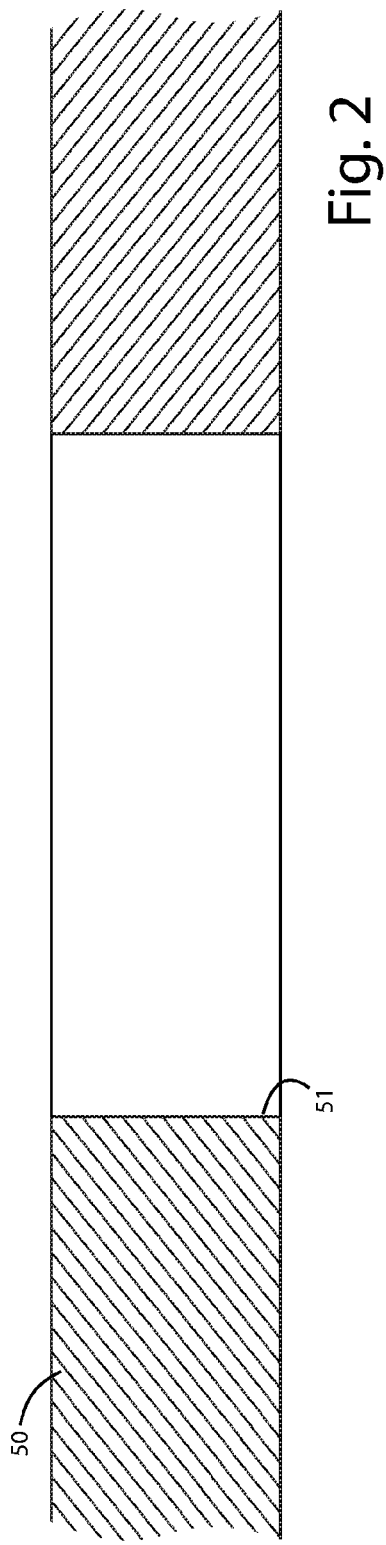

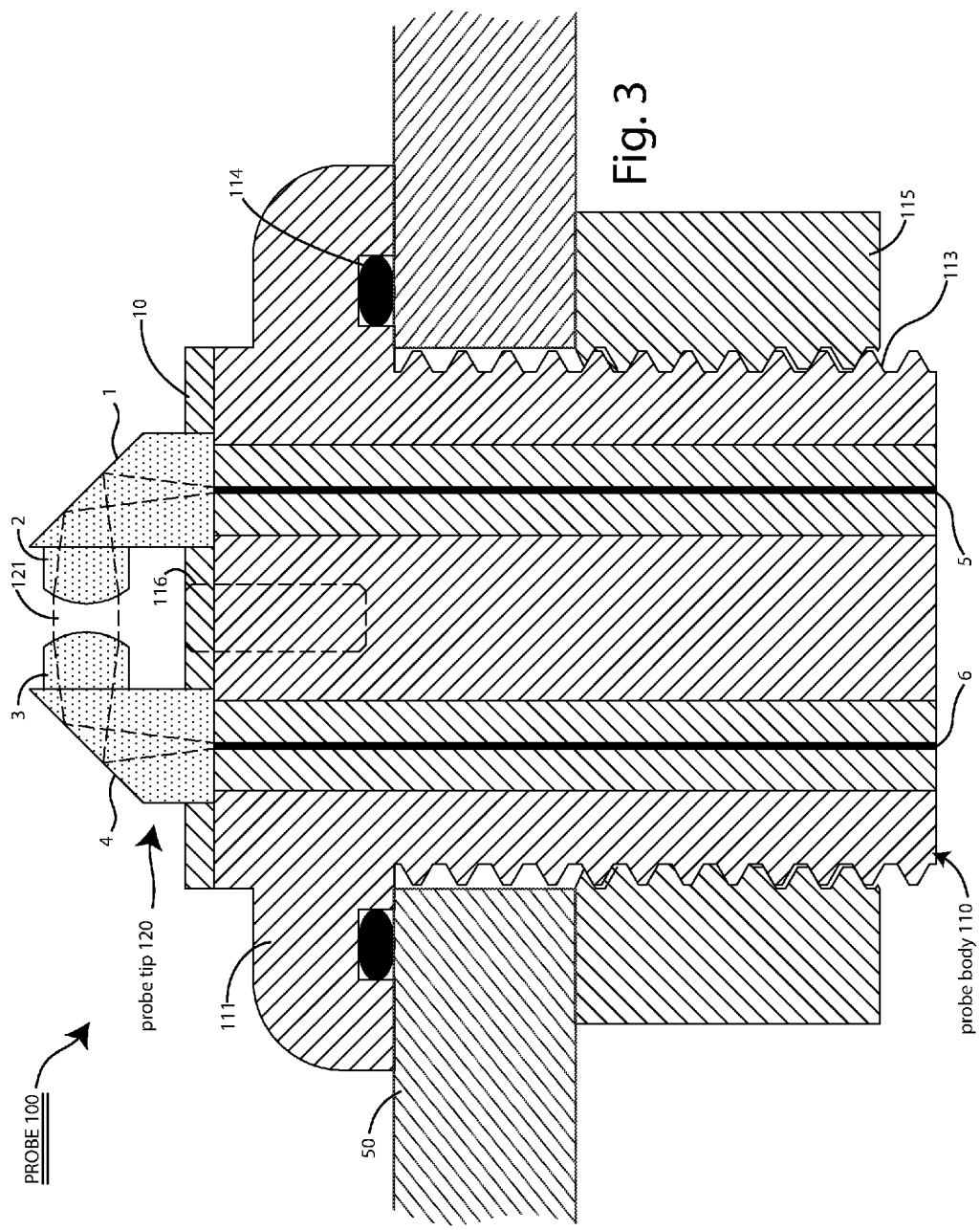

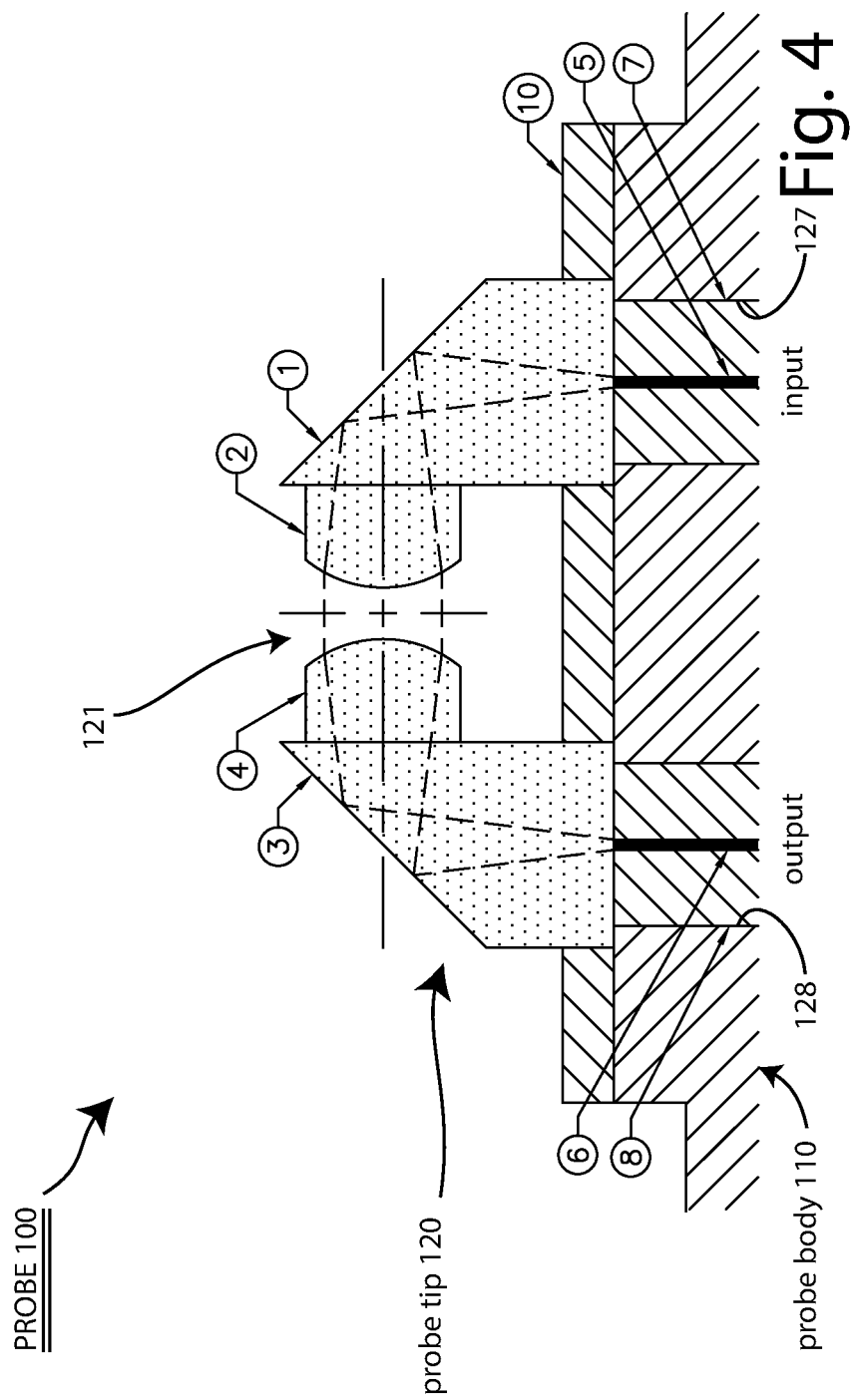

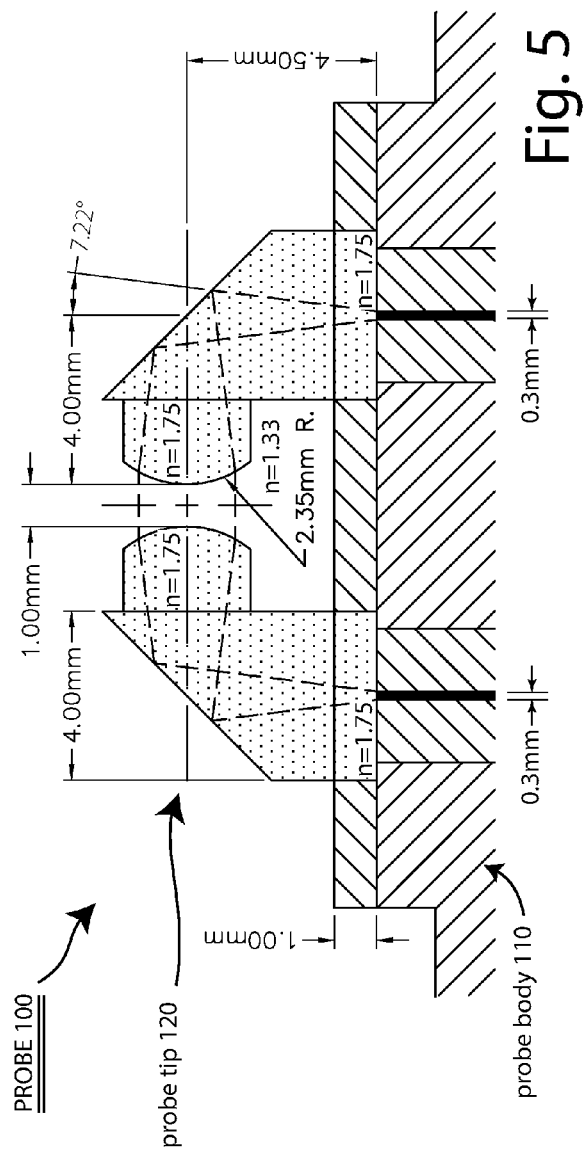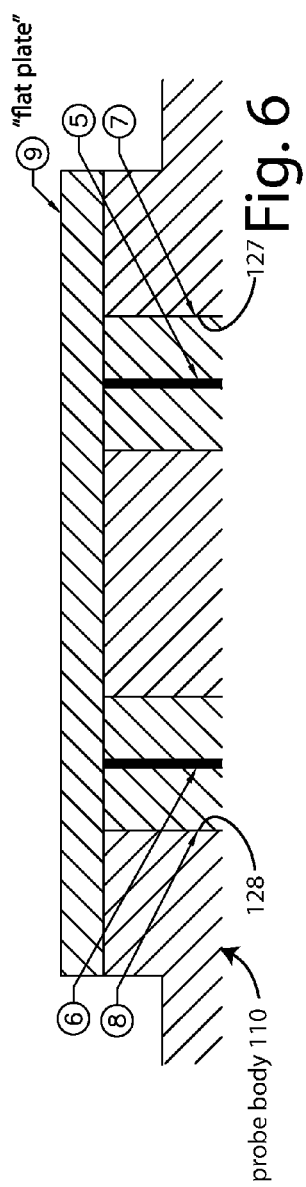

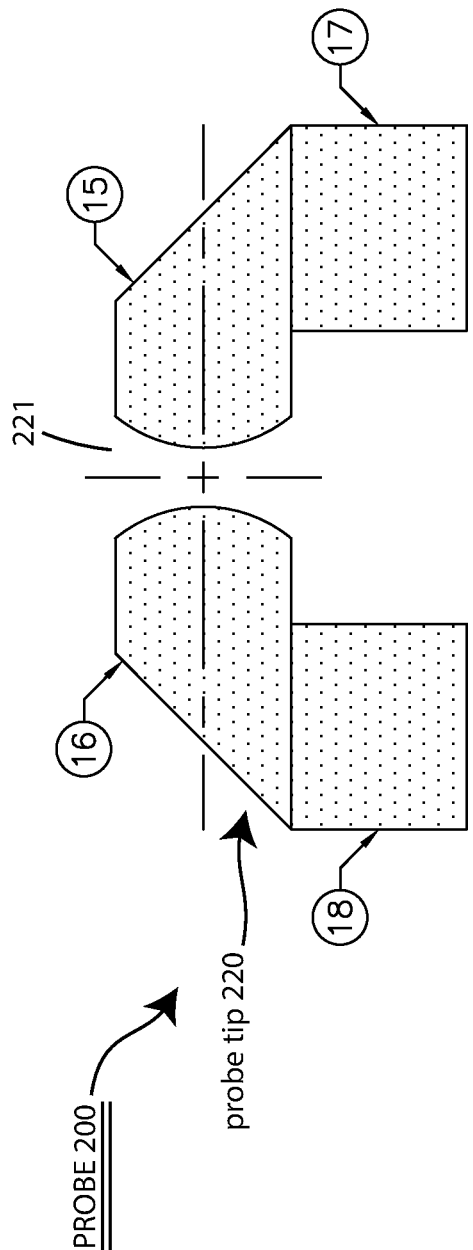

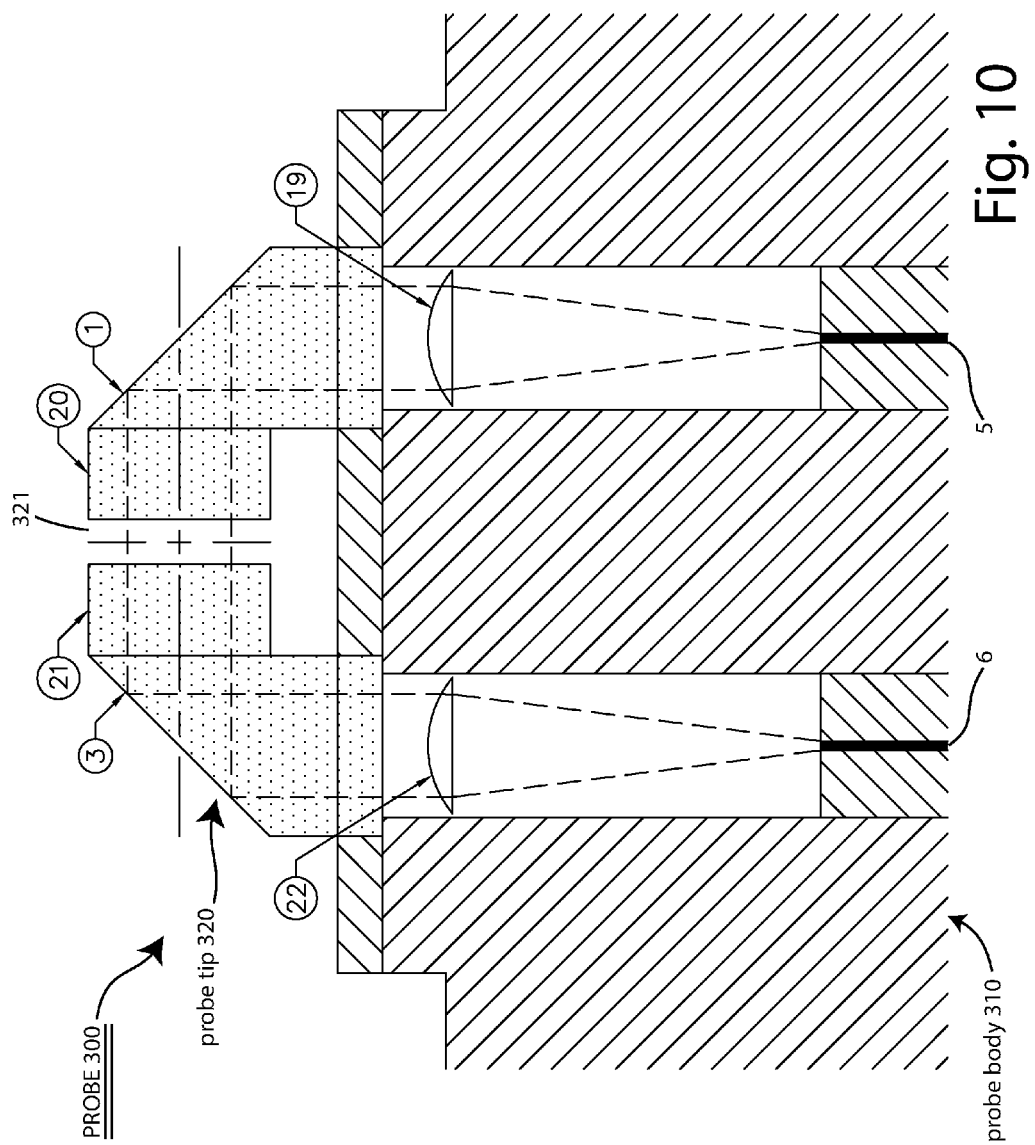

TRANSVERSE OPTICAL TRANSMISSION PROBE

CROSS REFERENCE TO RELATED APPLICATIONS

This application claims the benefit of U.S. Provisional Patent Application Ser. No. 62/089,525, filed Dec. 9, 2014.

BACKGROUND OF THE INVENTION

Field of the Invention

The invention relates generally to probes for spectroscopic measuring devices and, more particularly, to a transverse optical transmission probe.

Description of the Related Art

A variety of sampling devices are currently available for use in optical spectroscopy (primarily near-infrared and UV-visible). These generally use optical fibers to couple to an appropriate instrument. They fall into the following categories and suffer from the noted problems:
1. Single pass transmission probes. An example is the Axiom Analytical FPT-850. These probes provide high performance but involve numerous manufacturing steps and hence do not meet the low cost requirement of our invention.
2. Double pass transflectance probes. These probes are somewhat less expensive to produce than the single pass probes but have significant performance limitations. In particular, the sample gap needs to be one half of the desired pathlength thereby restricting sample flow.
3. Transmission cells. Commercial transmission cells are generally too costly for our current requirements. One could envision a less expensive cell. But it would be difficult to provide the serviceability required for the envisioned application with a transmission cell form factor.

There remains a need, therefore, for a transverse optical transmission probe that is compatible with water based samples, is capable of being produced at very low cost in substantial volume, has a relatively small sample gap but not so small that it causes sample retention in the sample gap and restricts sample flow; and is suitable for easy service and replacement in the field.

BRIEF SUMMARY OF THE INVENTION

The purpose of the invention is to provide a sample interfacing device for use with optical spectroscopy in the near-infrared, visible, and UV spectral regions, with the following objectives:

A relatively small sample gap, i.e. less than 10 mm and preferably around 1 mm;

Optimized flow characteristics so as to minimize sample retention in the sample gap;

Compatible with water based samples;

Capable of being produced at very low cost in substantial volume; and

Suitable for easy service and replacement in the field.

After considering the requirements for the envisioned application, we determined that a probe form factor was preferred in order to meet the requirement for serviceability. A probe can be inserted through the wall of the sample vessel through an appropriate seal and easily removed as a unit for service or replacement.

In its most general form, our invention includes the following:
1. The use of optical fibers to both transmit radiation from an instrument to the probe tip and to return the sample affected radiation to the instrument. Within the probe, these fibers would be parallel and contained in a single (preferably cylindrical) structure.
2. The use of, at most, two integrated optical elements protruding from the tip of the probe into the sample and configured so as to cause the incident radiation to pass through the sample in a direction transverse to the axis to the probe and to eventually reach the receiving fiber. Each of the optical elements may be formed from a single piece of material or may be a composite formed by adhering two or more pieces of material together.
3. The use of one or more lensed surfaces to cause the end of the transmitting fiber to be imaged on the end of the receiving fiber.

In accordance with the present invention, structures are disclosed which overcome the problems in the related art and achieve these objectives.

In a first aspect, the invention resides in a transverse optical transmission probe for analyzing a sample comprising: a probe body; first and second optical fibers in the probe body, each optical fiber having a distal end; a probe tip connected to the probe body; first and second optical elements in the probe tip that protrude into the sample and define a sample gap therebetween through which the sample passes; and wherein the first optical fiber is configured for transmitting radiation from an instrument to the probe tip and the second optical fiber returning sample affected radiation from the probe tip to the instrument. Said first optical element is configured for receiving the radiation transmitted by the first optical fiber and transmitting the radiation across the sample gap and through the sample to form the sample-affected radiation within the sample gap, said second optical element is configured for receiving the sample-affected radiation from the sample gap and transmitting the sample-affected radiation to the second optical fiber; and at least one lensed surface causes the distal end of the first optical fiber to be imaged onto the distal end of the second optical fiber.

The invention, now having been briefly summarized, may be better visualized by turning to the following drawings wherein like elements are referenced by like numerals.

DESCRIPTION OF THE DRAWINGS

The presently preferred embodiments of the just summarized invention can be best understood in connection with a detailed description of the following figures.

FIG. 1 shows a first preferred probe 100 comprised of a probe body 110 and a probe tip 120 having a sample gap 121;

FIG. 2 shows a process line or vessel having a wall 50 with an aperture 51;

FIG. 3 shows the probe 100 mounted in the wall 50 of the process line or vessel of FIG. 2 with a hex nut 115 used to compress an O-ring 114 against the wall 50;

FIG. 4 shows a distal portion of the first preferred probe 100 of FIG. 1, focusing in on the first preferred probe tip 110;

FIG. 5 is similar to FIG. 4 but includes some typical dimensions and the refractive index values used for components of the first preferred probe tip 120;

FIG. 6 shows how a flat plate is temporarily clamped against the end of the probe ferrules 7, 8 while the optical fibers 6, 7 are epoxied in place in order to assure that the ends of the optical fibers 6, 7 are in the same plane;

FIG. 9 shows a simplified portion of a second alternative probe 200 having an an alternative probe tip 220 where elements 15 and 16 incorporate both the lensed surfaces and the diagonal reflecting surfaces and elements 17 and 18 are simple rectangular blocks of optical material;

FIG. 10 shows a distal portion of a third alternative probe 300 having an alternative probe tip 320.

DETAILED DESCRIPTION OF THE PREFERRED EMBODIMENTS

Figure 8:
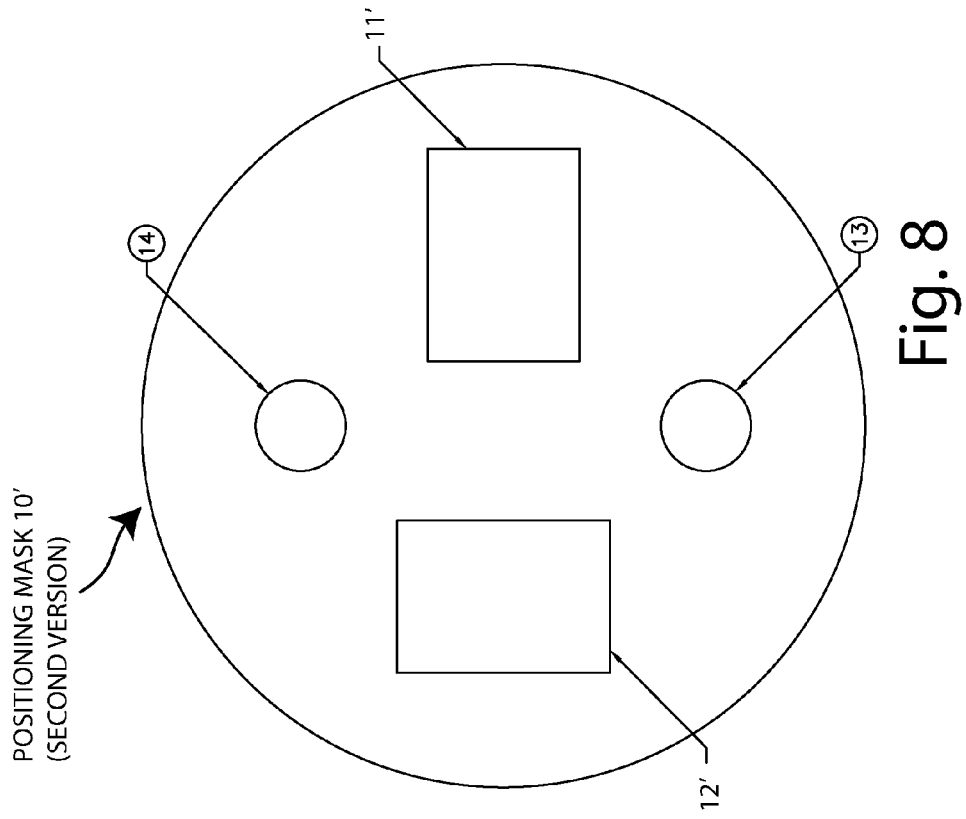
FIG. 8 shows a second version of a positioning mask 10' having rectangular cutouts 11', 12' that provide some additional space relative to the cross-sectional dimensions of the optical prisms 1,3.

The primary impetus for development of our invention has been a particular set of applications utilizing near-infrared vibrational spectroscopy. However, it can also be applied to other fields of optical spectroscopy.

(1) First Preferred Embodiment

FIG. 1 shows a first preferred probe 100 that is comprised of a probe body 110 and a probe tip 120 having a sample gap 121. The preferred probe body 110 has a shoulder 111 with an annular groove on its underside, and threads 113 along its length. The preferred probe tip 120 has a sample gap 121.

FIG. 2 shows a process line or vessel having a wall 50 with an aperture 51 for receiving the probe 100.

FIG. 3 provides additional details showing how the probe 100 could be mounted through the wall 50 of the sample vessel. As shown in FIG. 3, the preferred probe 100 is secured to the sample vessel's wall 50 with an O-ring 114 (e.g. a size 020 O-ring) compressed against the vessel's wall 50 between the probe body's shoulder 111 and a hex nut 115. This is just one example of many possible mechanisms for mounting the probe 100 with its probe tip 120 and related sample gap 121 exposed to the fluid to be analyzed.

FIG. 4 is a close-up view of a distal portion of the first preferred probe 100 of FIG. 1, focusing on the structure and operation of first preferred probe tip 120. In this particular embodiment, the inventors have chosen optical components 1, 2, 3, 4 so as to minimize cost and complexity. Since the anticipated samples will be water based and not strongly caustic, it is advantageously possible to adhere the various components together by using optical quality epoxy, thereby eliminating the need for any air gaps in the optical system. Note that the presence of air gaps would necessitate that these be sealed and hence would require a more complex (and expensive) mechanical structure.

FIG. 4 shows the optical components of the first preferred embodiment, namely items 1, 2, 3, and 4. We anticipate that, in large scale production, each of the pairs (1 and 2) and (3 and 4) could be molded as a single component. For prototyping and early stage production, each pair was comprised of a rectangular cross section prism (1 and 3) and a plano-convex lens (2 and 4). These shapes are desirable because they can easily be produced by typical optical polishing vendors. For reasons that will become apparent below, these optical components will be fabricated from materials having relatively high refractive indices. Examples might be sapphire and a high index glass such as SF11. In some embodiments, the index of refraction is greater than about 1.65, and in other embodiments the index of refraction is greater than about 1.5. In a presently preferred embodiment, the index of refraction is greater than 1.7 and less than about 1.8. In a presently preferred embodiment, the index of refraction is greater is about 1.75.

Optical radiation is introduced into the probe tip by means of one of a pair of optical fibers 5 and 6 which are contained in ferrules 7 and 8. For sake of this discussion, we will let 5 be the input fiber. A typical fiber will have a numeric aperture of 0.22. For this value, the light emerging from a distal end of the fiber will diverge with a half angle of about 12.7 degrees in air. Once the light enters the high index optical medium of item 1, the divergence angle will be reduced substantially (7.22 degrees for n=1.75), as shown in the Figure. The diverging light is reflected by a mirrored coating on the diagonal surface of prism 1 and is then directed to the convex surface of lens 2 where it is formed into a nominally collimated beam. After traversing the sample gap, the light is collected by the second lens 4, reflected by the second diagonal surface, and focused on a distal end of the receiving fiber, 6. As we have seen, the use of high refractive index optical materials minimizes the divergence angle thereby minimizes the required diameter of the lenses. It is also dictated by the fact that the lensed surfaces are in contact with the sample, which will typically have a refractive index around n=1.33.

FIG. 5 is similar to FIG. 4 but includes some typical dimensions and the refractive index values used for our illustration. For the initial prototypes, we plan to use sapphire for the prisms in order to maximize the transmission for the longer wavelength end of the near-IR region. Sapphire has a refractive index of refraction in the near-IR of about n=1.75. We also plan to use commercially available SF11 glass lenses which have a refractive index in the near-IR of about n=1.785. We have selected an available lens design that allows us to conveniently image the end of the input fiber on the end of the receiving fiber. Each fiber is assumed to have a core diameter of 0.3 mm. In other embodiments, the fibers may have a different core diameter, e.g. 0.2 mm.

In FIG. 5, the minimum sample gap 121 has been chosen to be 1 mm. Since the curved surfaces of the two lenses 2, 4 are in contract with the sample, the actual sample gap will vary across the surface. However, the data nonlinearity introduce by this variation can easily be dealt with by performing separate analyses for regions of high and low water absorption. The chosen dimensions provide for free liquid flow around the lenses 2, 4 so as to discourage sample retention and enhance cleaning. For example, if the gap between the cylindrical surfaces of the lenses and the positioning mask were 1 mm or less—rather than the 2 mm shown in the figures—there would be a tendency for viscous samples to collect in this region.

(2) Practical Mechanical Considerations

So far we have described an idealized optical design for our invention. However, there are additional practical considerations. In particular, the optical elements 1,2 and 3,4 need to be aligned so as to accurately image the end of the input fiber 5 on that of the receiving fiber 6. As presently preferred, the mounting hardware (and assembly jigs) are designed to passively align the optics as closely as possible.

However, we presently believe that it will necessary to allow for some additional final active alignment while the optical elements are being epoxied together. The mechanical discussion below includes a couple of ways that this can be accomplished.

The first mechanical requirement for assembly of the probe 100 is to assure that the ends of the optical fibers 5, 6 are in the same plane. FIG. 6 illustrates a presently preferred method of how this can be accomplished. The fibers 5, 6 are terminated in cylindrical ferrules 7, 8. These will be free to slide through corresponding and parallel bores 127, 128 in the probe body 110. To mount the fibers 5, 6 in the probe body 110, we will clamp a flat plate 9 against the end of the probe body 110. The fiber containing ferrules 7, 8 are slid into the bores 127, 128 of the probe body 110 until they contact the plate 9 and then epoxied in place. The plate 9 is then removed.

Figure 7:
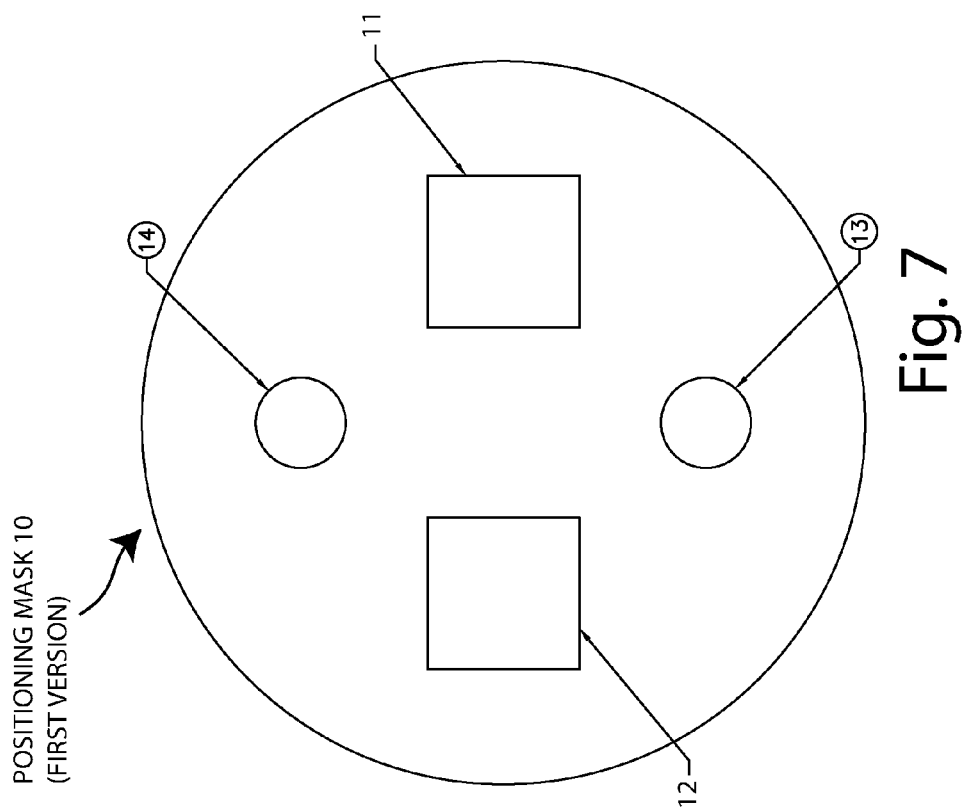
FIG. 7 shows a first version of a positioning mask 10 having precise rectangular cutouts 11, 12 that closely conform to the cross-sectional dimensions of the optical prisms 1,3.

The next step is to assemble the probe tip 120 by mounting and properly aligning the optical elements 1, 2 and 3, 4 on the end of the probe body 110. We presently foresee at least two possible approaches to doing this. Both of these would employ a positioning mask 10 on the end of the probe. FIGS. 7 and 8 show two presently preferred positioning masks 10 and 10'.

In FIG. 7, the first positioning mask 10 has precise rectangular cutouts 11, 12 matched as closely as possible to the cross-sectional dimensions of the optical prisms 1, 3. The prisms 1,3 are simply inserted through these cutouts 11, 12 and adhered to a distal end of the probe body 110, in contact with the ends of the two fibers 5, 6, using an optically transparent epoxy. The other two holes, 13 and 14, are used to accommodate pins 115 that are positioned in the probe body 110 (see FIG. 1) for accurately locating the mask 10 in a desired registration with the distal end of the probe body 110.

The positioning mask 10 provides passive mechanical alignment, but it may not achieve the desired optical alignment and some form of active alignment may be needed. One way to accomplish this is to leave at least one of the lenses 2, 4 to be mounted and actively positioned after the mounting of the prisms 1 and 3. We can then connect the fibers 5, 6 to an instrument and monitor the signal level as the lens(es) is/are positioned. The lens(es) 2, 4 would then be adhered in place by using UV curing epoxy.

FIG. 8 shows a second version of a positioning mask 10' that is suitable for dynamic alignment. The second positioning mask 10' features rectangular cutouts 11', 12' that provide additional space relative to the cross-sectional dimensions of the optical prisms 1, 3. The additional space is used to move the optical prisms 1, 3 before adhering them in their final position with the UV curing epoxy.

In FIG. 8, the illustrated cutouts 11, 12 are slightly elongated in transverse axes, but other arrangements may be possible. Using the second version of the positioning mask 10', we would mount the lenses 2, 4 on the prisms 1, 3 before mounting the prisms 1, 3 to the probe body 110. The prisms 1, 3 would then be positioned so as to maximize the signal. To facilitate this dynamic mounting, the cutouts 13', 14' are elongated in transverse directions so that one prism 1 could slide in the X direction and the other prism 2 in the Y direction.

(3) Other Possible Embodiments

FIG. 9 shows a second alternative probe 200, in greatly simplified presentation, that is based on a second alternative probe tip 220 have a simple modification relative to the first preferred probe tip 120 (other elements have been omitted for simplicity of presentation). The probe tip 220 provides sample gap 321. In this design, elements 15 and 16 incorporate both the lensed surfaces and the diagonal reflecting surfaces. Elements 17 and 18 are simple rectangular blocks of optical material. The function of this design would be the same as that of FIG. 1. However, it would be more expensive to fabricate in small quantities since it would not use a commercially available lens.

FIG. 10 shows a third alternative probe 300 that has lenses 19, 22 mounted below the prisms 1, 3, within the probe body 110, to eliminate the need for lensed surfaces in contact with the sample. Here, lens 19 collects the light diverging from the input fiber 5 and forms it into a collimated beam (dashed lines). Prisms 1 and 3 are the same as in FIGS. 1 to 5. Elements 20 and 21, however, have parallel optical faces and cross sections which can be either circular or rectangular. Lens 22 focuses the collimated light onto the receiving fiber 6.

This third design 300 has the advantage of eliminating the pathlength variation across the sample gap 321. However, it has the disadvantage of requiring a more complicated mechanical structure. In addition, it introduces the possibility of sample leakage into the necessary air gaps associated with the lenses 21, 22 located within the probe body 310.

Figure 11:
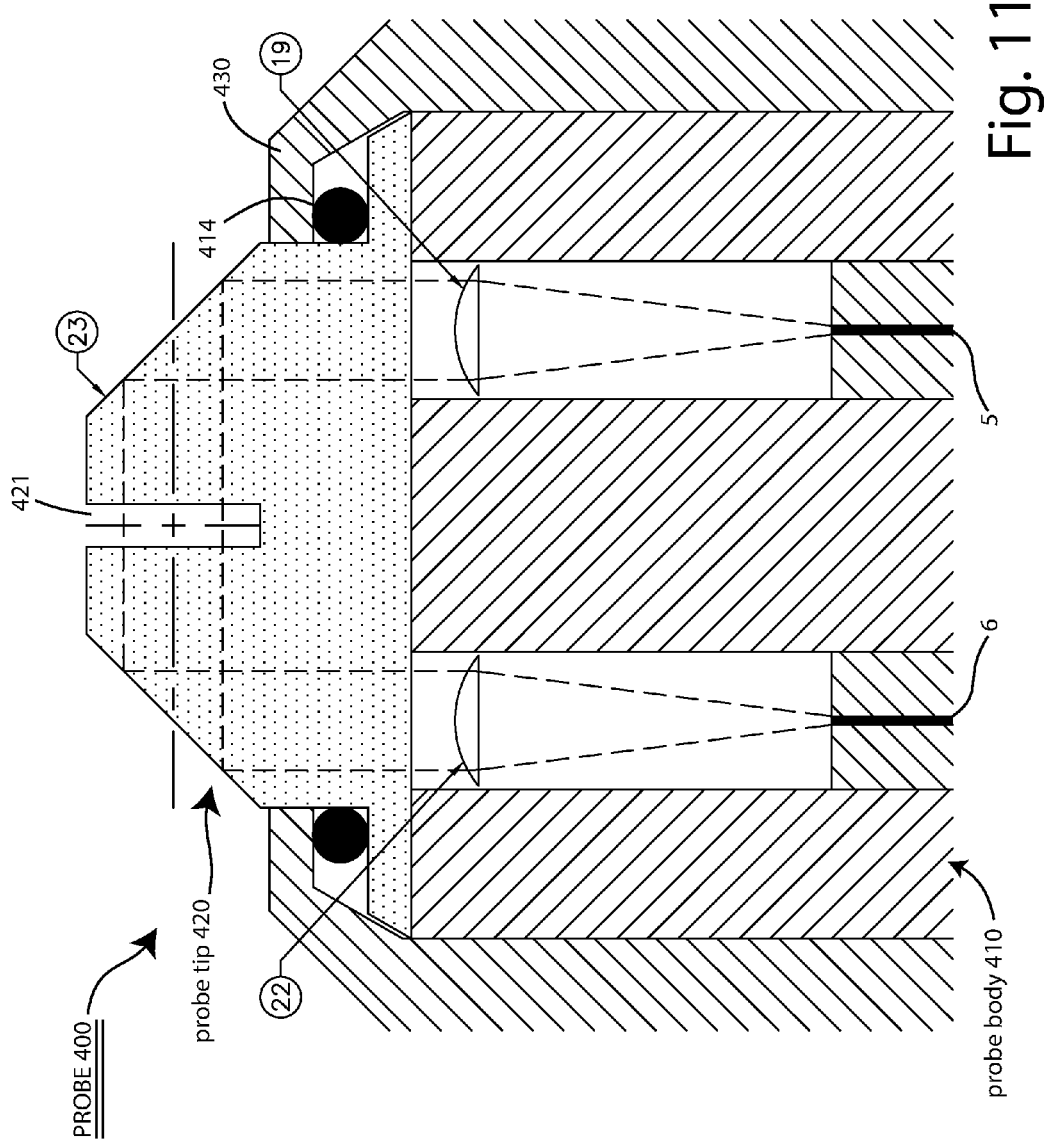
FIG. 11 shows a distal portion of a fourth alternative probe 400 having an alternative probe tip 420.

FIG. 11 illustrates a fourth alternative 400 having a probe tip 410 with a sample gap 421 according to a further alternative design. In this design, the probe tip 410 comprises a sample contacting optical element, 23, that is fabricated as a single component having a circular cross section in the region of contact with the probe body 410. In principle, this design could use an O-ring 414 or similar seal to interface an annular shoulder of the probe tip 420 to the probe body 410 with a suitable compression collar 430, thereby eliminating the need for epoxy in contact with the sample. This design would be quite difficult to fabricate using conventional polishing methods but might be amenable to molding with appropriate tooling.

Many alterations and modifications may be made by those having ordinary skill in the art without departing from the spirit and scope of the invention. Therefore, it must be understood that the illustrated embodiments have been set forth only for the purposes of example and that it should not be taken as limiting the invention as defined by the following claims. The claims are thus to be understood to include the specifically illustrated and described embodiments, structures based on equivalents concepts, and substitutions that incorporate the invention.

The invention claimed is:

1. A transverse optical transmission probe for analyzing a sample comprising:
   a probe body;
   first and second optical fibers in the probe body, each optical fiber having a distal end,
   a probe tip connected to the probe body;
   first and second optical elements in the probe tip that protrude into the sample and define a sample gap therebetween through which the sample passes;
   the first optical fiber configured for transmitting radiation from an instrument to the probe tip and the second optical fiber returning sample affected radiation from the probe tip to the instrument;
   said first optical element configured for receiving the radiation transmitted by the first optical fiber and transmitting the radiation across the sample gap and through the sample to form the sample-affected radiation within the sample gap, said second optical element configured for receiving the sample-affected radiation from the sample gap and transmitting the sample-affected radiation to the second optical fiber; and at least one lensed surface that causes the distal end of the first optical fiber to be imaged onto the distal end of the second optical fiber.

2. The transverse optical transmission probe of claim 1 wherein, the probe tip is configured such that a line extending between the probe body and the probe tip defines an axis of the probe and wherein the first optical element is configured so as to cause the incident radiation to pass through the sample in a direction that is substantially transverse to the axis of the probe before being received by the second optical element.

3. The transverse optical transmission probe of claim 1 wherein the first optical element is formed by adhering together two or more pieces of material and wherein the second optical element is formed by adhering together two or more pieces of material.

4. The transverse optical transmission probe of claim 3 wherein the pieces of optical material are adhered together with optical quality epoxy.

5. The transverse optical transmission probe of claim 3 wherein the probe further comprises a positioning mask at a distal end of the probe body, the positioning mask having a first aperture that precisely aligns a proximal end of the first optical element with the first optical fiber and having a second aperture that precisely aligns a proximal end of the second optical elements with the second optical fiber, to provide for passive mechanical alignment during assembly.

6. The transverse optical transmission probe of claim 3 wherein the probe further comprises a positioning mask at a distal end of the probe body, the positioning mask having a first aperture that aligns a proximal end of the first optical element with the first optical fiber and having a second aperture that aligns a proximal end of the second optical elements with the second optical fiber, wherein at least one of the first and second apertures is larger than the proximal end of the first and second optical element, respectively, in at least one dimension, to provide for active alignment during assembly.

7. The transverse optical transmission probe of claim 1 wherein the first optical element is formed from a single piece of material and wherein the second optical element is formed from a single piece of material.

8. The transverse optical transmission probe of claim 7 wherein the probe further comprises a positioning mask at a distal end of the probe body, the positioning mask having a first aperture that precisely aligns a proximal end of the first optical element with the first optical fiber and having a second aperture that precisely aligns a proximal end of the second optical elements with the second optical fiber, to provide for passive mechanical alignment during assembly.

9. The transverse optical transmission probe of claim 7 wherein the probe further comprises a positioning mask at a distal end of the probe body, the positioning mask having a first aperture that aligns a proximal end of the first optical element with the first optical fiber and having a second aperture that aligns a proximal end of the second optical elements with the second optical fiber, wherein at least one of the first and second apertures is larger than the proximal end of the first and second optical element, respectively, in at least one dimension, to provide for active alignment during assembly.

10. The transverse optical transmission probe of claim 1 wherein the first and second optical elements are collectively formed from a single piece of material.

11. The transverse optical transmission probe of claim 1 wherein the first optical element comprises a diagonal surface with a mirrored coating that reflects radiation from the first optical fiber across the sample gap; and
wherein the second optical element comprises a diagonal surface with a mirrored coating that reflects sample-affected radiation toward the second optical fiber.

12. The transverse optical transmission probe of claim 11 wherein at least one lensed surface comprises first and second convex surface on either side of the sample gap, the first convex surface provided as part of the first optical element and the second convex surface provided as part of the second optical element.

13. The transverse optical transmission probe of claim 1 wherein the first and second optical elements are formed of high refractive index material having an index of refraction that is greater than about 1.5.

14. The transverse optical transmission probe of claim 13 wherein the first and second optical elements are formed of high refractive index material having an index of refraction that is greater than about 1.7 and less than about 1.8.

15. The transverse optical transmission probe of claim 14 wherein the first and second optical elements are formed of high refractive index material having an index of refraction of about 1.75.

16. The transverse optical transmission probe of claim 1 wherein the first and second optical elements are comprised of sapphire.

17. The transverse optical transmission probe of claim 1 wherein the first and second optical elements are comprised of sapphire or a high index glass such as SF11.

18. The transverse optical transmission probe of claim 1 wherein the sample gap is sufficiently wide as to permit free sample flow.

19. The transverse optical transmission probe of claim 18 wherein the sample gap is less than about 10 mm.

20. The transverse optical transmission probe of claim 18 wherein the sample gap is about 1 mm.

21. The transverse optical transmission probe of claim 1 wherein the probe body comprises a sufficiently elongated extension for insertion through an aperture in a wall of a process line or sample vessel, wherein the elongated extension comprises external threads, and further comprising a hex nut for attaching the probe body to the process line or sample vessel with the probe tip situated inside of the process line or sample vessel for contact with the sample.

22. The transverse optical transmission probe of claim 1 wherein the probe body comprises first and second bores and further comprising first and second cylindrical ferrules that receive the first and second optical fibers and fit within the first and second bores.

23. The transverse optical transmission probe of claim 22 wherein the first and second optical fibers and first and second ferrules are secured in the first and second bores with epoxy with the distal ends of the first and second optical fiber in the same plane.

* * * * *